(12) United States Patent
Hopkinson et al.

(10) Patent No.: US 10,086,173 B2
(45) Date of Patent: Oct. 2, 2018

(54) BALLOON CATHETER SYSTEMS AND METHODS

(71) Applicant: Merit Medical Systems, Inc., South Jordan, UT (US)

(72) Inventors: Aaron J. Hopkinson, Herriman, UT (US); Kevin Oberg, Clinton, MS (US); Barton P. Gill, Salt Lake City, UT (US); Hugh W. Goldston, West Jordan, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 268 days.

(21) Appl. No.: 14/341,203

(22) Filed: Jul. 25, 2014

(65) Prior Publication Data

US 2015/0032049 A1    Jan. 29, 2015

Related U.S. Application Data

(60) Provisional application No. 61/858,451, filed on Jul. 25, 2013.

(51) Int. Cl.
*A61M 25/10* (2013.01)
*A61M 25/00* (2006.01)
(Continued)

(52) U.S. Cl.
CPC .......... *A61M 25/10* (2013.01); *A61M 25/005* (2013.01); *A61M 25/0032* (2013.01); *A61M 25/0097* (2013.01); *A61M 25/002* (2013.01);
*A61M 25/0052* (2013.01); *A61M 25/09041* (2013.01); *A61M 25/1006* (2013.01);
(Continued)

(58) Field of Classification Search
CPC .......... A61M 25/0026; A61M 25/0032; A61M 25/0052; A61M 25/01; A61M 25/10; A61M 25/104; A61M 2025/004; A61M 2025/1056; A61M 2025/1061
See application file for complete search history.

(56) References Cited

U.S. PATENT DOCUMENTS

| 4,976,690 A | 12/1990 | Solar et al. |
| 5,087,246 A | 2/1992 | Smith |

(Continued)

FOREIGN PATENT DOCUMENTS

| EP | 0344530 | 5/1989 |
| EP | 0528294 | 8/1992 |

(Continued)

OTHER PUBLICATIONS

International Search Report and Written Opinion dated Nov. 5, 2014 for PCT/US2014/048193.

(Continued)

*Primary Examiner* — Kami A Bosworth
(74) *Attorney, Agent, or Firm* — Stoel Rives LLP

(57) ABSTRACT

The embodiments disclosed herein relate to balloon catheter assemblies. The balloon catheter assemblies can include a plurality of ports, a junction hub, an elongated member, and an inflation balloon. The balloon catheter assemblies can also include a reinforced tubular shaft extending through the inflation balloon. The balloon catheter assemblies can also include a retaining mechanism that can be removably attached to the junction hub.

16 Claims, 16 Drawing Sheets

(51) Int. Cl.
*A61M 25/09* (2006.01)
*A61M 25/01* (2006.01)

(52) U.S. Cl.
CPC ............... *A61M 2025/0059* (2013.01); *A61M 2025/0063* (2013.01); *A61M 2025/0177* (2013.01); *A61M 2025/1056* (2013.01); *A61M 2025/1061* (2013.01)

(56) References Cited

U.S. PATENT DOCUMENTS

| | | | |
|---|---|---|---|
| 5,171,222 | A | 12/1992 | Euteneuer et al. |
| 5,318,529 | A | 6/1994 | Kontos |
| 5,423,754 | A * | 6/1995 | Cornelius ............ A61M 25/104 604/103 |
| 5,476,477 | A * | 12/1995 | Burns ................. A61M 25/104 604/264 |
| 5,480,383 | A * | 1/1996 | Bagaoisan ........ A61M 25/0054 600/585 |
| 5,569,184 | A * | 10/1996 | Crocker ..................... A61F 2/88 604/103.01 |
| 5,728,063 | A * | 3/1998 | Preissman ............ A61M 25/005 604/103.09 |
| 5,746,745 | A | 5/1998 | Abele et al. |
| 5,820,613 | A * | 10/1998 | Van Werven-Franssen ................. A61M 25/104 604/103.09 |
| 5,906,606 | A * | 5/1999 | Chee ................... A61M 25/005 604/246 |
| 6,146,354 | A | 11/2000 | Beil |
| 6,280,545 | B1 | 8/2001 | Kanesaka |
| 6,322,534 | B1 | 11/2001 | Shkolnik |
| 8,690,824 | B2 | 4/2014 | Holman et al. |
| 2002/0068922 | A1 | 6/2002 | Peters |
| 2002/0111584 | A1 * | 8/2002 | Walker ................. A61M 25/00 604/113 |
| 2003/0014008 | A1 | 1/2003 | Jacques |
| 2004/0039369 | A1 | 2/2004 | Shelso |
| 2004/0092867 | A1 | 5/2004 | Murray |
| 2004/0092868 | A1 | 5/2004 | Murray |
| 2004/0236366 | A1 | 11/2004 | Kennedy, II et al. |
| 2005/0107821 | A1 | 5/2005 | Shanley et al. |
| 2005/0137617 | A1 | 6/2005 | Kelley et al. |
| 2005/0288628 | A1 | 12/2005 | Jordan et al. |
| 2007/0129748 | A1 | 6/2007 | Eidenschink et al. |
| 2007/0270935 | A1 * | 11/2007 | Newhauser ............. A61F 2/954 623/1.11 |
| 2007/0288053 | A1 | 12/2007 | Trotta |
| 2010/0030141 | A1 | 2/2010 | Chermoni |
| 2011/0288478 | A1 * | 11/2011 | Ehrenreich ..... A61M 25/10181 604/99.04 |
| 2012/0209176 | A1 | 8/2012 | Anderson |
| 2013/0197563 | A1 | 8/2013 | Saab et al. |

FOREIGN PATENT DOCUMENTS

| | | |
|---|---|---|
| EP | 0611582 | 1/1994 |
| EP | 2170452 | 1/2009 |
| WO | 2004101059 | 6/2012 |
| WO | PCT/US2014/048193 | 7/2014 |
| WO | PCT/US2014/048204 | 7/2014 |

OTHER PUBLICATIONS

International Search Report and Written Opinion dated Nov. 11, 2014 for PCT/US2014/048204.
U.S. Appl. No. 14/341,261, filed Jul. 25, 2014, Hopkinson et al.
Office Action dated Feb. 2, 2017 for U.S. Appl. No. 14/341,261.
European Search Report dated Jun. 21, 2017 for EP14829001.8.
Office Action dated May 22, 2017 for U.S. Appl. No. 14/341,261.
European Search Report dated Mar. 20, 2017 for EP14829001.8.
Office Action dated Sep. 28, 2017 for U.S. Appl. No. 14/341,261.
Office Action dated Feb. 27, 2018 for U.S. Appl. No. 14/341,261.

* cited by examiner

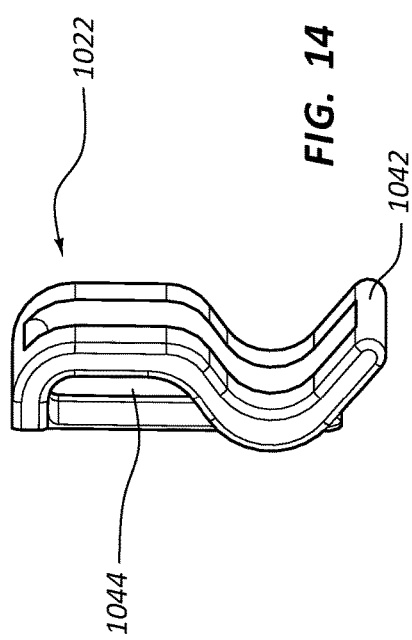
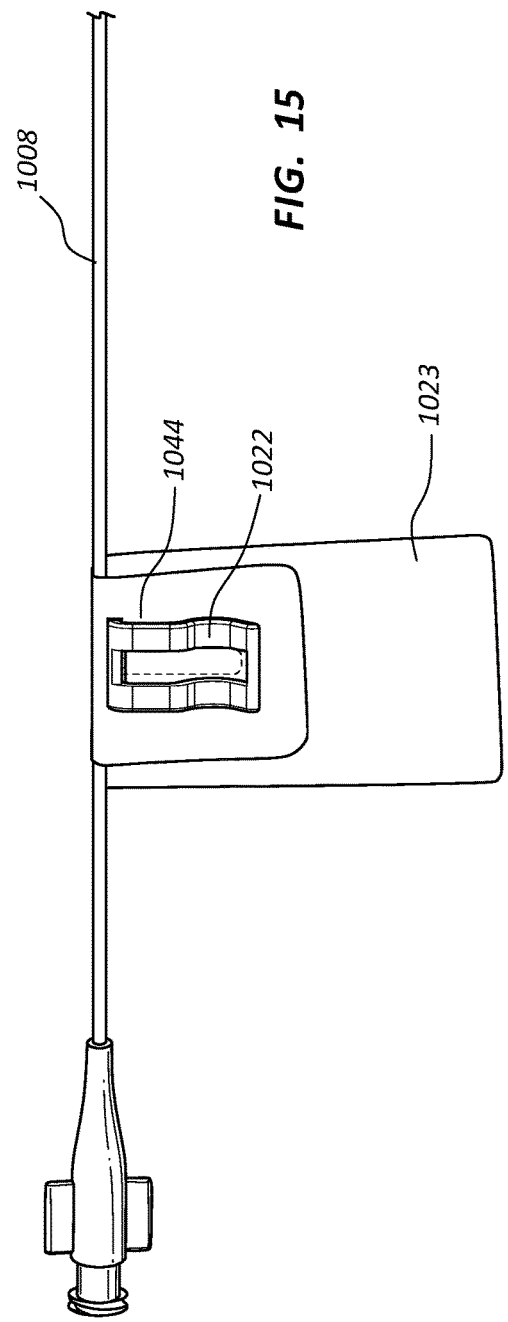

BALLOON CATHETER SYSTEMS AND METHODS

RELATED APPLICATIONS

This application claims priority to U.S. Provisional Application No. 61/858,451, filed on Jul. 25, 2013, titled BALLOON CATHETER SYSTEMS AND METHODS, which is hereby incorporated by reference in its entirety.

TECHNICAL FIELD

The present disclosure relates generally to catheters. More specifically, the present disclosure relates to balloon catheter assemblies and methods of use.

BRIEF DESCRIPTION OF THE DRAWINGS

The embodiments disclosed herein will become more fully apparent from the following description and appended claims, taken in conjunction with the accompanying drawings. While various aspects of the embodiments are presented in drawings, the drawings depict only typical embodiments, which will be described with additional specificity and detail through use of the accompanying drawings in which:

FIG. 14 is a perspective view of a retaining mechanism of a balloon catheter assembly, according to another embodiment of the present disclosure.

FIG. 15 is a side view of an assembly comprising the retaining mechanism of FIG. 14 and a portion of a balloon catheter assembly in a first configuration.

DETAILED DESCRIPTION

Figure 1:
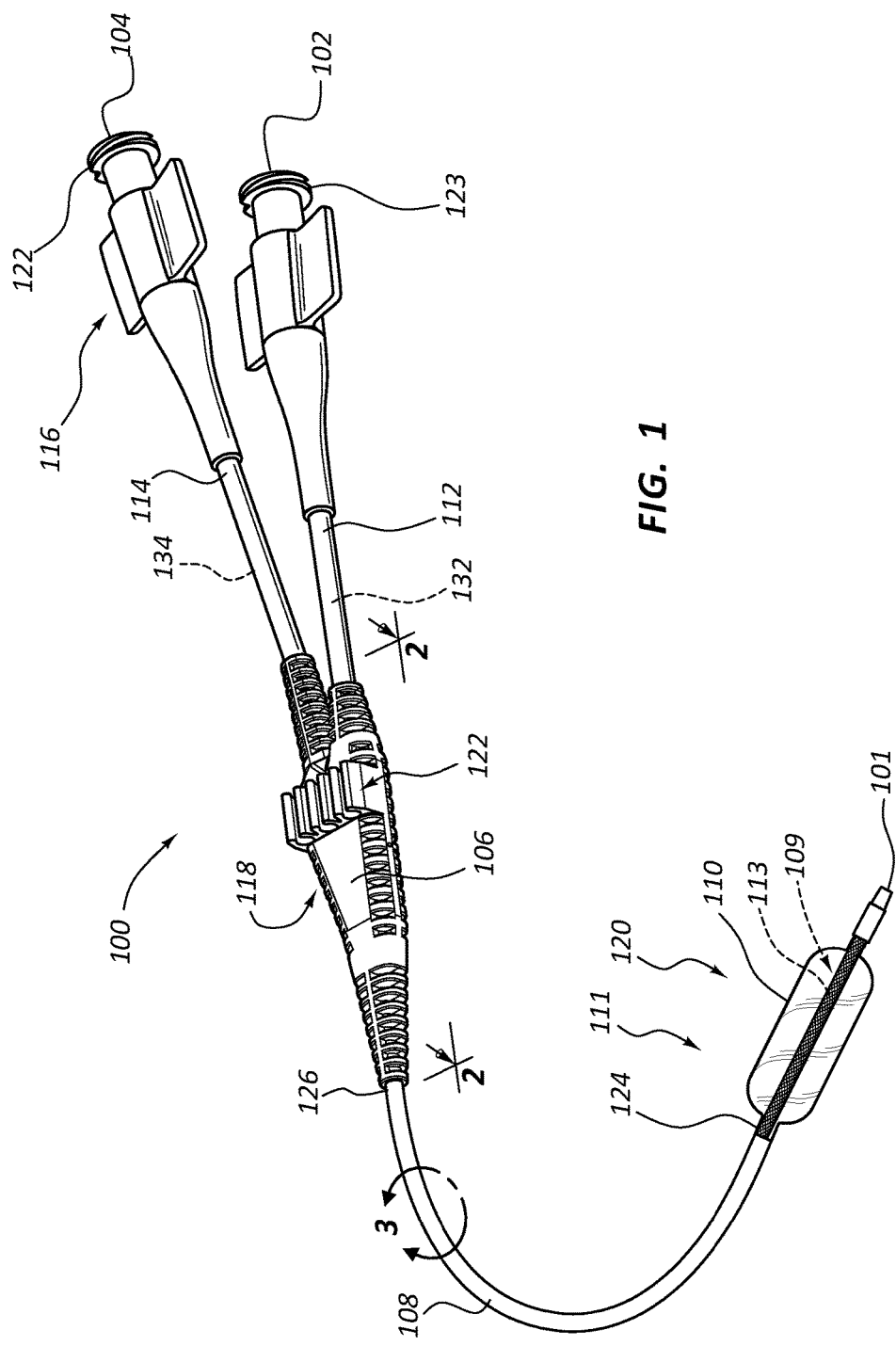
FIG. 1 is a perspective view of a balloon catheter assembly, according to one embodiment of the present disclosure.

The various embodiments disclosed herein generally relate to catheters. More specifically, the various embodiments relate to balloon catheter systems, for example, balloon catheter assemblies, and related methods. In some embodiments, the balloon catheter assembly comprises a plurality of ports, a junction hub, an elongated member, and an inflation balloon. The balloon catheter assembly may further comprise one or more extension members. In some embodiments, the elongated member comprises a plurality of lumens extending therethrough. For example, the elongated member may comprise a guide wire lumen and two or more inflation/deflation lumens. The two or more inflation/deflation lumens may provide increased flow through the elongated member as compared to traditional balloon catheter assemblies. The two or more inflation/deflation lumens may also provide the elongated member with increased stiffness and rigidity.

Further disclosed herein are embodiments in which the balloon segment of a balloon catheter assembly comprises a tubular shaft extending through the inflation balloon. The tubular shaft may comprise a reinforcement member. The reinforcement member may provide rigidity and structural support to the tubular shaft and/or the balloon segment.

Further disclosed herein are embodiments directed toward a retaining mechanism. The retaining mechanism is configured to retain catheter tubing prior to and/or after use by a practitioner. In some embodiments, the retaining mechanism is disposed on a junction hub. In some embodiments, the retaining mechanism is removably attached to a junction hub.

It will be appreciated by one of skill in the art having the benefit of this disclosure that various features are sometimes grouped together in a single embodiment, figure, or description thereof for the purpose of streamlining the disclosure. Many of these features may be used alone and/or in combination with one another. It will further be appreciated by one of skill in the art having the benefit of this disclosure that many of the features disclosed herein may be used in conjunction with other catheter assemblies presently known or hereafter developed.

Embodiments may be understood by reference to the drawings, wherein like parts are designated by like numerals throughout. It will be understood by one of skill in the art having the benefit of this disclosure that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail. While the various aspects of the embodiments are presented in drawings, the drawings are not necessarily drawn to scale unless specifically indicated.

The phrases "coupled to" and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device, including the devices disclosed herein. As used herein, the proximal portion of a medical device is the portion nearest a practitioner during use, while the distal portion is a portion at the opposite end. For example, the proximal end of a balloon catheter assembly is defined as the end closest to the practitioner during insertion or utilization of the balloon catheter assembly. The distal end is the end opposite the proximal end, along the longitudinal direction of the balloon catheter assembly.

FIG. 1 illustrates a balloon catheter assembly 100 according to one embodiment of the present disclosure. The balloon catheter assembly 100 comprises a plurality of ports 102, 104, a junction hub 106, an elongated member 108, and an inflation balloon 110. In the illustrated embodiment, the balloon catheter assembly 100 further comprises one or more extension members 112, 114.

The ports 102, 104 are disposed at the proximal portion 116 of the balloon catheter assembly 100. The ports 102, 104 are configured for use in introducing and/or withdrawing various components and/or substances from the balloon catheter assembly 100. In the illustrated embodiment, a first port 102 is configured for use in introducing and/or removing a guide wire. For example, a guide wire may be inserted and/or extended through the first port 102, through the junction hub 106, through the elongated member 108, and through the inflation balloon 110 during use by a practitioner. In such embodiments, the first port 102 may be referred to as a guide wire port. In some embodiments, the guide wire may further be extended out of and beyond the distal end 101 of the balloon catheter assembly 100.

In the illustrated embodiment, a second port 104 is configured for use in introducing and/or removing inflation fluid (e.g., gas, liquid, etc.). The inflation fluid is configured for use in inflating the inflation balloon 110. In such embodiments, the second port 104 may be referred to as an inflation/deflation port 104.

As further illustrated in FIG. 1, the ports 102, 104 may extend through additional hubs, fittings, and/or connectors 122, 123, such as luer connectors, which may also be disposed at the proximal portion 116 of the balloon catheter assembly 100.

The extension members 112, 114 may be configured to longitudinally extend the plurality of ports 102, 104 away from the junction hub 106. The one or more extension members 112, 114 each comprise a lumen 132, 134 extending longitudinally therethrough. The lumen 132, 134 within each extension member 112, 114 provides a passageway for components and/or substances (e.g., a guide wire and/or inflation fluid) between the ports 102, 104 and the junction hub 106. In some embodiments, the extension members 112, 114 comprise a polymeric material.

The junction hub 106 is disposed at an intermediate portion 118 of the balloon catheter assembly 100. The junction hub 106 may be coupled to the extension members 112, 114. Further, as illustrated in FIG. 1, the junction hub 106 may be configured to couple the extension members 112, 114 and/or ports 102, 104 to the elongated member 108. In some embodiments, the junction hub 106 comprises a retaining mechanism 122.

The elongated member 108 is configured to provide a passageway for components and/or substances between the junction hub 106 and the inflation balloon 110 and/or the distal end 101 of the balloon catheter assembly 100. For example, in the illustrated embodiment, the distal end 124 of the elongated member 108 is coupled to the balloon segment 111, which comprises the inflation balloon 110. And the proximal end 126 of the elongated member 108 is coupled to the junction hub 106.

In some embodiments, the elongated member 108 comprises a plurality of lumens extending longitudinally therethrough. For example, the illustrated elongated member 108 comprises a first lumen that is configured to receive a guide wire. The first lumen is further configured to serve as a passageway through which the guide wire may be inserted and/or extended. In such embodiments, the first lumen may be referred to as a guide wire lumen.

The elongated member 108 also comprises a second lumen and a third lumen. The second and third lumens are configured to serve as passageways through which inflation fluid may be introduced into and/or withdrawn from the inflation balloon 110. In such embodiments, the second and third lumens may be referred to as inflation/deflation lumens. Further details of the first, second, and third lumens of the balloon catheter assembly 100 are discussed below.

In some embodiments, the elongated member 108 comprises a polymeric material. The polymeric material may be extruded to form the elongated member 108 using one or more extrusion techniques. The elongated member 108 may also be referred to as catheter tubing, an elongated tubular member, or a tubular member.

The inflation balloon 110 is disposed at the distal portion 120 of the balloon catheter assembly 100. The interior of the inflation balloon 110 is in fluid communication with the second and third lumens of the elongated member 108 (i.e., the inflation/deflation lumens). The interior of the inflation balloon 110 is also in fluid communication with the inflation/deflation port 104. For example, inflation fluid may flow between the inflation/deflation port 104, the inflation/deflation lumens of the elongated member 108, and the inflation balloon 110 (or interior thereof) during both the inflation and the deflation procedures.

In some embodiments, a tubular shaft 109 extends through the inflation balloon 110. Together, the tubular shaft 109 and the inflation balloon 110 may comprise part of a balloon segment 111 that is coupled to the elongated member 108. The tubular shaft 109 may comprise a reinforcement member 113. The reinforcement member 113 is configured to provide stiffness, rigidity, and/or structural support to the tubular shaft 109 and/or the distal portion 120 of the balloon catheter assembly 100.

In some embodiments, the tubular shaft 109 comprises a lumen extending longitudinally therethrough. The lumen of the tubular shaft 109 may be in fluid communication with the first lumen of the elongated member 108 (i.e., the guide wire lumen). The lumen of the tubular shaft 109 may also be in fluid communication with the guide wire port 102. For example, a guide wire may be extended through the guide wire port 102, through the guide wire lumen of the elongated member 108, and through the lumen of the tubular shaft 109. In some embodiments, the guide wire may be further extended through and beyond the distal end 101 of the balloon catheter assembly 100. Additional details of the tubular shaft 109 and reinforcement member 113 are discussed below.

Figure 2:
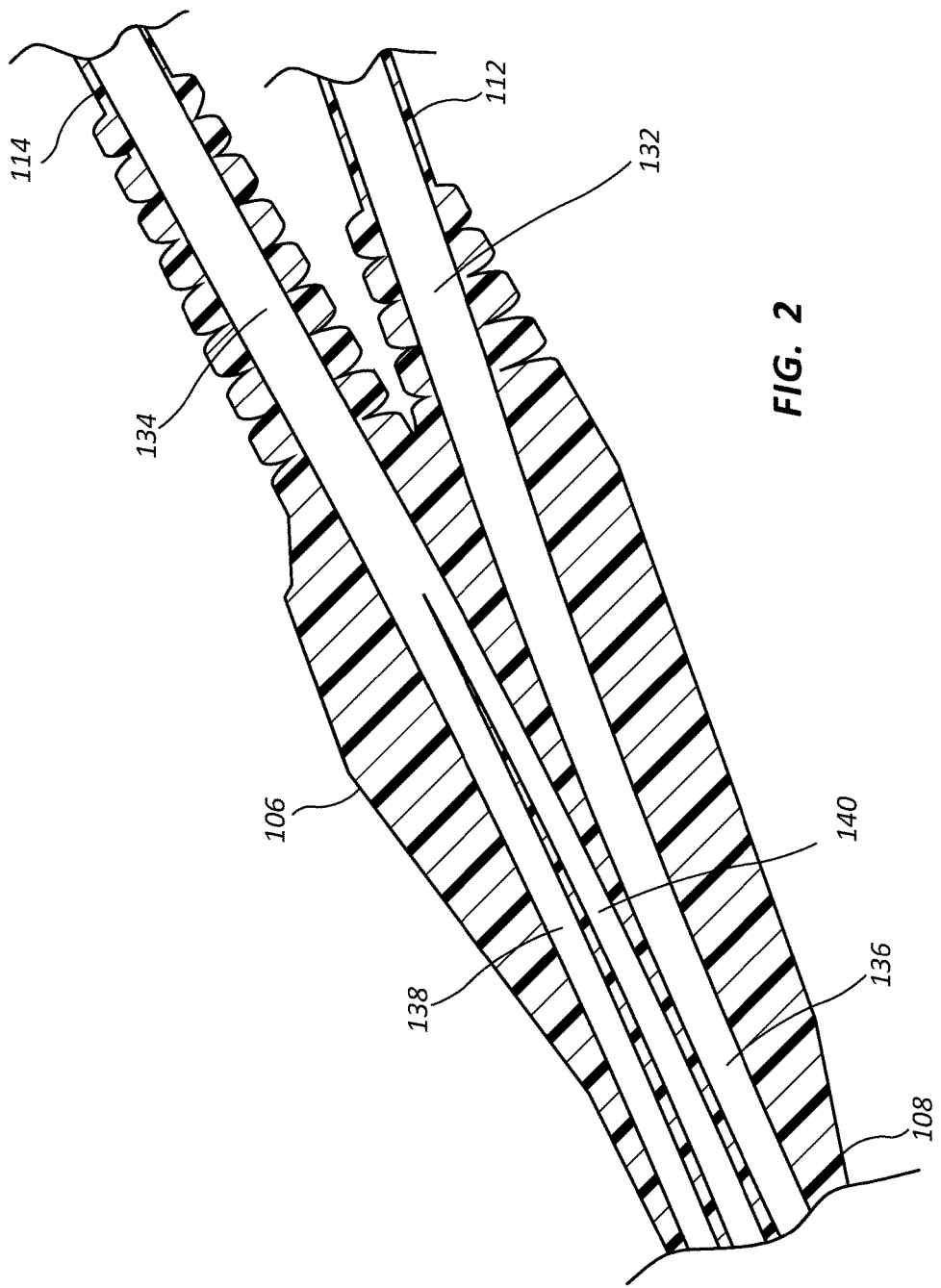
FIG. 2 is a cross-sectional view of the junction hub of the balloon catheter assembly of FIG. 1 taken through line 2-2.

FIG. 2 illustrates a cross-section of the junction hub 106 of the balloon catheter assembly 100 of FIG. 1, taken through line 2-2. As shown in FIG. 2, the extension members 112, 114 each comprise a single lumen 132, 134, and the elongated member 108 comprises a plurality of lumens 136, 138, 140. Further, the lumens 132, 134 of the extension members 112, 114 are coupled to one or more lumens 136, 138, 140 of the elongated member 108. In other words, the lumens 132, 134 of the extension members 112, 114 are in fluid communication with one or more lumens 136, 138, 140 of the elongated member 108 via the junction hub 106. For example, in the illustrated embodiment, the lumen 134 of the extension member 114 is in fluid communication with lumens 138 and 140.

The junction hub 106 is also configured such that a first port (e.g., a guide wire port) may be in fluid communication with a first lumen 136 (e.g., a guide wire lumen) of the elongated member 108. For example, a first port may be in fluid communication with lumen 132 of extension member 112, which is also in fluid communication with first lumen 136 of the elongated member 108.

The junction hub 106 is also configured such that a second port (e.g., an inflation/deflation port) may be in fluid communication with second and third lumens 138, 140 (e.g., inflation/deflation lumens) of the elongated member 108. For example, a second port may be in fluid communication with lumen 134 of extension member 114, which is also in fluid communication with second and third lumens 138, 140 of the elongated member 108.

The junction hub 106 may comprise a polymeric material. In some embodiments, the junction hub 106 is injection-molded. For example, a plurality of mandrels may be disposed into the various lumens 136, 138, 140 of a previously extruded elongated member 108. The plurality of mandrels may further be disposed into the extension members 112, 114. For example, in forming the junction hub 106 of the illustrated embodiment, a single mandrel is extended between the first lumen 136 of the elongated member 108 and the lumen 132 of the extension member 112. Two individual and separate mandrels are extended between the second and third lumens 138, 140 of the elongated member 108 and the lumen 134 of the extension member 114. With the mandrels placed, the junction hub 106 may be molded into shape. After the molded junction hub 106 is cooled, the mandrels are removed.

Figure 3:
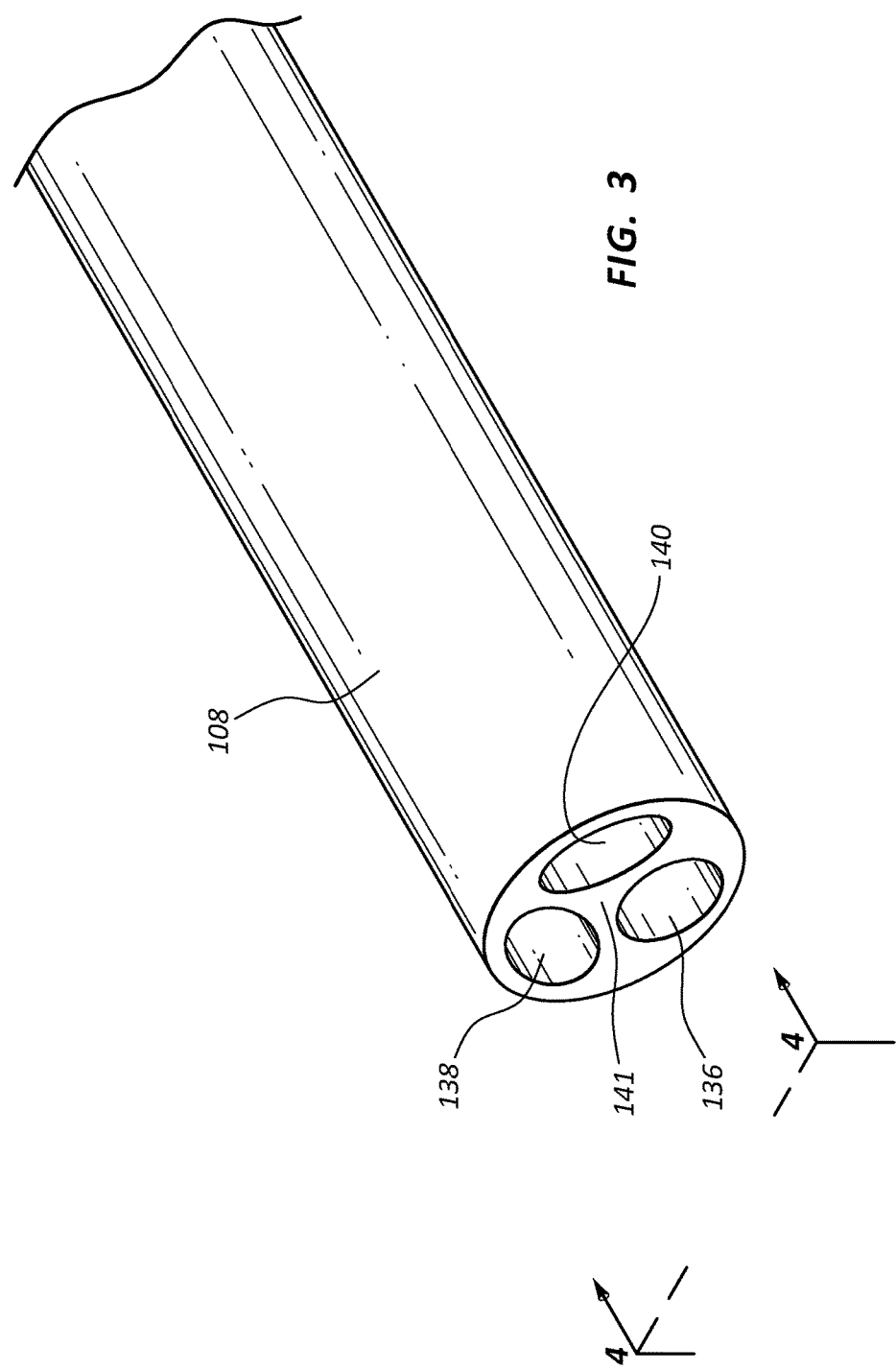
FIG. 3 is a cut-away view of a portion of the elongated member of the balloon catheter assembly of FIG. 1 taken through line 3.

FIG. 3 is a cut-away view of a portion the elongated member 108 of the balloon catheter assembly 100 of FIG. 1 taken through line 3.

As shown therein, the elongated member 108 comprises a plurality of lumens 136, 138, 140. More specifically, the elongated member 108 comprises a first lumen 136 which is configured to serve as a guide wire lumen, and second and third lumens 138, 140 which are configured to serve as inflation/deflation lumens. The plurality of lumens 136, 138, 140 may extend the entire longitudinal length of the elongated member 108. Further, the first lumen 136 may not be in fluid communication with the second and third lumens 138, 140 at any point along the assembly.

The elongated member 108 is flexible. However, in some embodiments, the elongated member 108 exhibits increased rigidity, stiffness, and/or kink resistance due to the geometry and positioning of the lumens 136, 138, 140 when compared to designs with different geometries. For example, the elongated member 108 is extruded such that polymeric material 141 is disposed around and between each lumen 136, 138, 140. The structural support from the polymeric material 141 provides increased rigidity and/or stiffness to the elongated member 108, which may provide the elongated member 108 with increased kink resistance, pushability, and/or torqueability. Notwithstanding the increased rigidity and/or stiffness, the elongated member 108 may still be configured to be flexible such that it may bend when advanced to a target site during therapy. In other words, the elongated member 108 is configured to be sufficiently flexible to be advanced along the working channel of an endoscope or within a body lumen, while also configured to distribute loads and forces to resist kinking, collapse of the lumens, or other undesired deformation. The design can thus eliminate the presence of weak spots or load concentrations.

Figure 4:
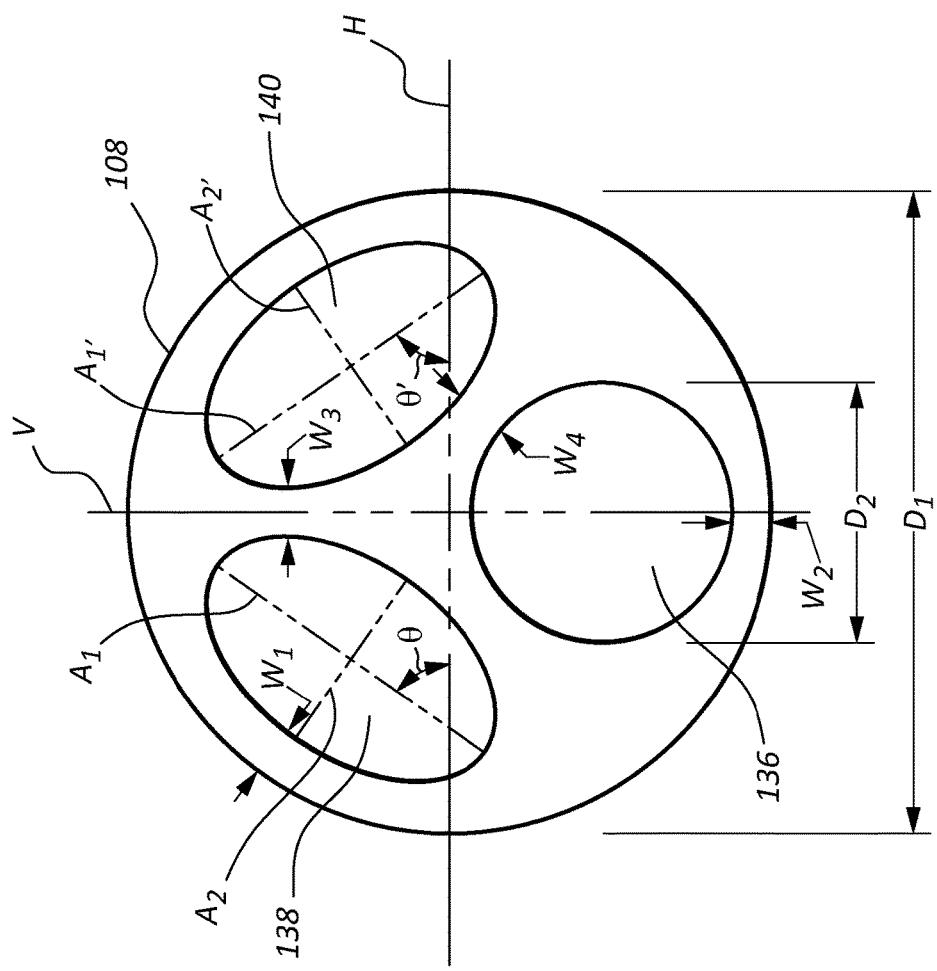
FIG. 4 is a cross-sectional view of the elongated member of the balloon catheter assembly of FIG. 3 taken through line 4-4.

FIG. 4 illustrates a cross-section of the elongated member 108 of the balloon catheter assembly 100 of FIGS. 1 and 3, taken through line 4-4 of FIG. 3. In the illustrated embodiment, the cross-section of the elongated member 108 is substantially circular in shape. Other shapes may be used. The cross-section of the first lumen 136 (i.e., the guide wire lumen) is also substantially circular in shape. The cross-sections of the second and third lumens 138, 140 (i.e., the inflation/deflation lumens) are substantially oval in shape. In other embodiments, the cross-sections of the second and third lumens 138, 140 may be substantially kidney shaped. In yet other embodiments, the cross-sections of the second and third lumens 138, 140 may be substantially semi-circle shaped. In still other embodiments, the cross-sections of the second and third lumens 138, 140 may be substantially semi-oval shaped. Other shapes may be used as desired.

In some embodiments, modifying the size and/or shape of the lumens 136, 138, 140 may alter the characteristics of the elongated member 108. For example, in some embodiments, substantially oval shaped or kidney shaped inflation/deflation lumens 138, 140 may accommodate higher flow of inflation fluid through the elongated member 108 as compared to other shapes. Modifying the size and/or shape of one or more of the lumens 136, 138, 140 may also affect the rigidity and/or stiffness of the elongated member 108. For example, increasing the size of one or more of the lumens 136, 138, 140 may result in a decreased amount of polymeric material 141 disposed throughout the elongated member 108, which may decrease the rigidity and/or stiffness of the elongated member 108. Similarly, decreasing the size of one or more of the lumens 136, 138, 140 may result in an increased amount of polymeric material 141 disposed throughout the elongated member 108, which may increase the rigidity and/or stiffness of the elongated member 108.

In the embodiment of FIG. 4, a vertical axis V and horizontal axis H of the cross-section are indicated. These axes are disposed perpendicular to each other. In the illustrated embodiment, the cross-section of the elongated member 108 is substantially circular and the axes V and H intersect at the center of the circular cross-section. The diameter $D_1$ of the circular cross-section is also indicated. The first lumen 136 is also substantially circular in cross-section, with a diameter of $D_2$. The first lumen 136 is centered along the vertical axis V in the illustrated embodiment.

Additionally, in the embodiment of FIG. 4, the second 138 and third 140 lumens are elliptical, with major axes $A_1$ and $A_1'$ and minor axes $A_2$ and $A_2'$ marked. In the illustrated embodiment, the second 138 and third 140 lumens are disposed such that their major axes $A_1$ and $A_1'$ are disposed at angles θ and θ'. In the illustrated embodiment, the second 138 and third 140 lumens are disposed such that θ and θ' have the same value; in other embodiments, these angles may be different.

Various wall thicknesses are also indicated in FIG. 4. Specifically, $W_1$ indicates the minimum thickness between the second lumen 138 and the outside wall of the elongated member 108. In some embodiments an equivalent minimum thickness for the third lumen 140 may have the same value as $W_1$. $W_2$ indicates the minimum thickness between the first lumen 136 and the outside wall of the elongated member 108. $W_3$ indicates the minimum distance between the second and third lumens. $W_4$ indicates the minimum distance between the first and third lumens. The minimum distance between the second and first lumens may have the same value as $W_4$.

The geometry and arrangement of the lumens 136, 138, 140 of the elongated member 108 may reduce the tendency of the elongated member 108 to kink or otherwise deform in an undesired manner. The elongated member 108 may be designed such that it is flexible enough for advancement along working channels (i.e., an endoscope working channel) or within body lumens, while sufficiently resilient to resist kinking. Further, these properties may be considered while still maintaining a low-profile catheter, or a catheter with a minimum diameter $D_1$. The elongated member 108 may thus be configured to distribute loads to reduce deformation and kinking, while retaining flexibility and sufficient lumen size to accommodate guide wires, desired flow rates, and so forth.

In some embodiments θ and θ' may be equal, while in other embodiments they may be different. θ and θ' may be from about 30° to about 60°, including from about 40° to about 50°. Additionally, the second 138 and third 140 lumens may or may not be disposed such that they intersect the horizontal axis H of the cross-section.

The wall thicknesses $W_1$, $W_2$, $W_3$, and $W_4$ may be tailored to provide strength while accommodating lumens of desired size. In some embodiments, each wall thickness may be no less than 6%, no less than 10%, or no less than 15% of the value of the diameter $D_1$ of the elongated member 108. The lumens also may be sized to accommodate instruments and flow without compromising kink resistance. In some embodiments, the diameter $D_2$ of the first lumen may be no more than 50%, no more than 45%, or no more than 40% of the value of the diameter $D_1$ of the elongated member. The minor axes $A_2$ and $A_2'$ of the second 138 and third 140 lumens may be no more than 30%, no more than 40%, or no more than 50% of the value of the diameter $D_1$ of the elongated member. Finally, the relative sizes of the lumens 136, 138, 140 may also be tailored. In some embodiments, the sum of an area circumscribed by the cross-section of the second lumen 138 and an area circumscribed by the cross-section of the third lumen 140 may be between 1.4 and 2 times an area circumscribed by the cross-section of the first lumen 136.

Various absolute ranges for these values are within the scope of this disclosure, depending on the intended use and application of the assembly. Without limiting the disclosure to specific values, in some embodiments $D_1$ may be from about 0.03 inch to about 0.15 inch; $D_2$ may be from about 0.01 inch to about 0.05 inch; $W_1$, $W_2$, $W_3$, and $W_4$ may each be from about 0.003 inch to about 0.012 inch; $A_1$ and $A_1'$ may be from about 0.020 inch to about 0.055 inch; and $A_2$ and $A_2'$ may be from about 0.010 inch to about 0.040 inch.

In some embodiments, the disclosed balloon catheter assemblies comprising multiple inflation/deflation lumens exhibit increased flow rates as compared to traditional balloon catheter assemblies. For example, in some embodiments, a balloon catheter assembly comprising two inflation/deflation lumens may increase flow of inflation fluid by 10-15% or more when compared to a balloon catheter assembly consisting of only one inflation/deflation lumen. Increased flow of the inflation fluid decreases both inflation and deflation times during a medical procedure.

In some embodiments, the disclosed balloon catheter assemblies comprising multiple inflation/deflation lumens provide redundant inflation and/or deflation. For example, in some instances an inflation/deflation lumen may become kinked and/or blocked, and flow of the inflation fluid may be substantially restricted. In such instances, flow of the inflation fluid may nevertheless continue through an additional (i.e., second or third, etc.) inflation/deflation lumen.

Figure 5:
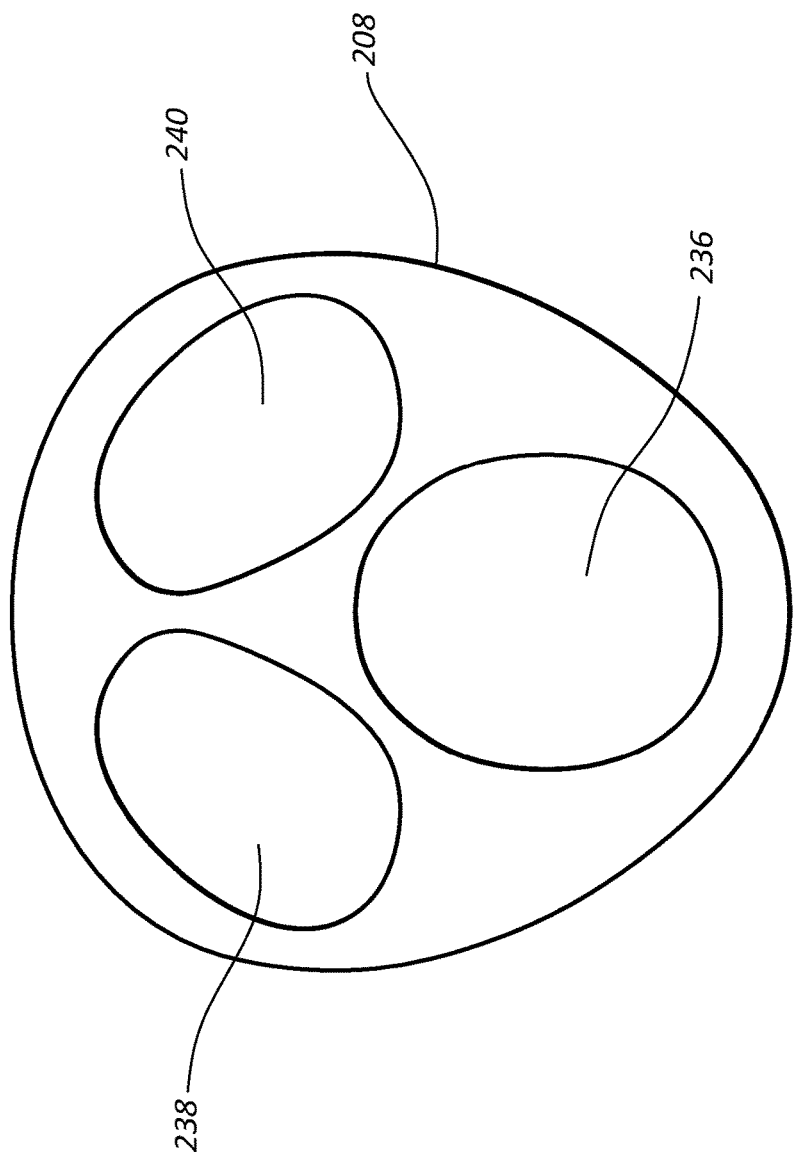
FIG. 5 is a cross-sectional view of an elongated member of a balloon catheter assembly, according to another embodiment of the present disclosure.
Figure 6:
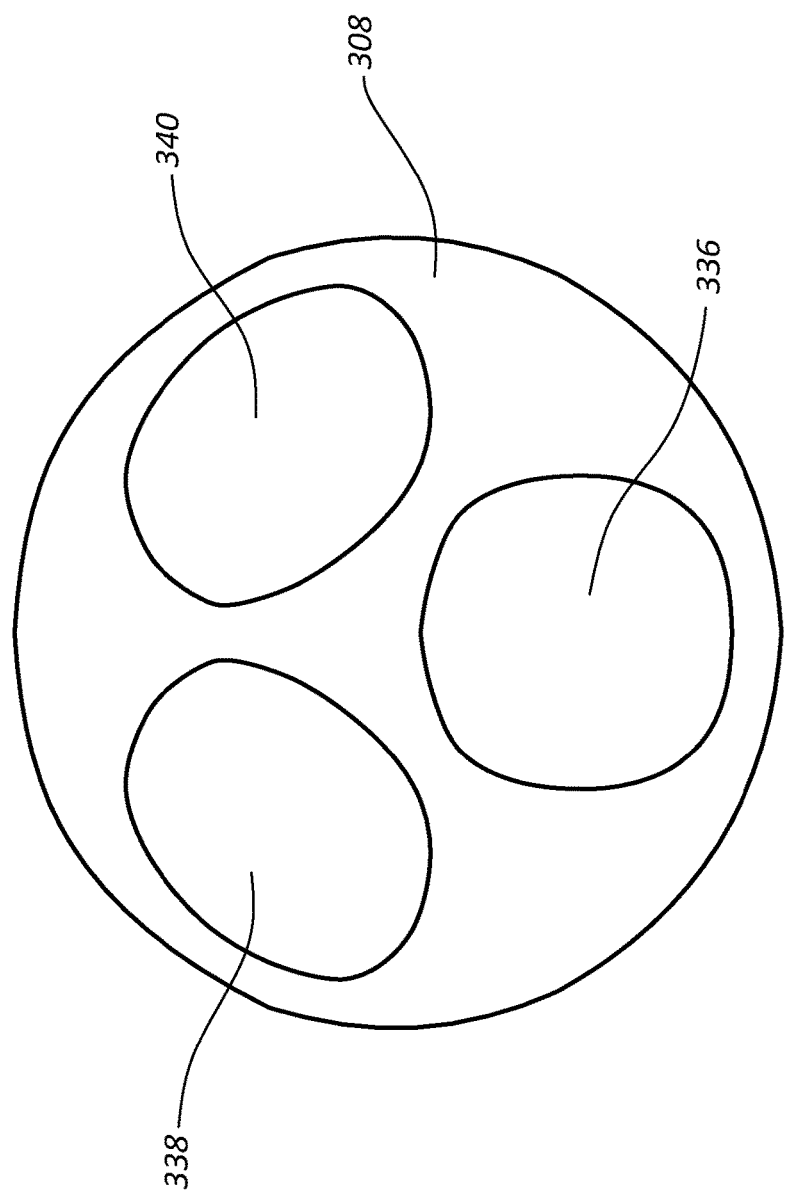
FIG. 6 is a cross-sectional view of an elongated member of a balloon catheter assembly, according to yet another embodiment of the present disclosure.

FIG. 5 is a cross-sectional view of an elongated member 208 of a balloon catheter assembly, according to another embodiment of the present disclosure, and FIG. 6 is a cross-sectional view of an elongated member 308 of a balloon catheter assembly, according to yet another embodiment of the present disclosure. FIGS. 5 and 6 illustrate variations in the shapes and sizes of the elongated member 208, 308 and/or lumens 236, 238, 240, 336, 338, 340. The shapes and/or sizes of the elongated member 208, 308, and/or lumens 236, 238, 240, 336, 338, 340 may vary based on several parameters, including the size of the guide wire, the type of catheter, the desired rate of inflation/deflation, and/or the desired rigidity or stiffness of the balloon catheter assembly.

Figure 7:
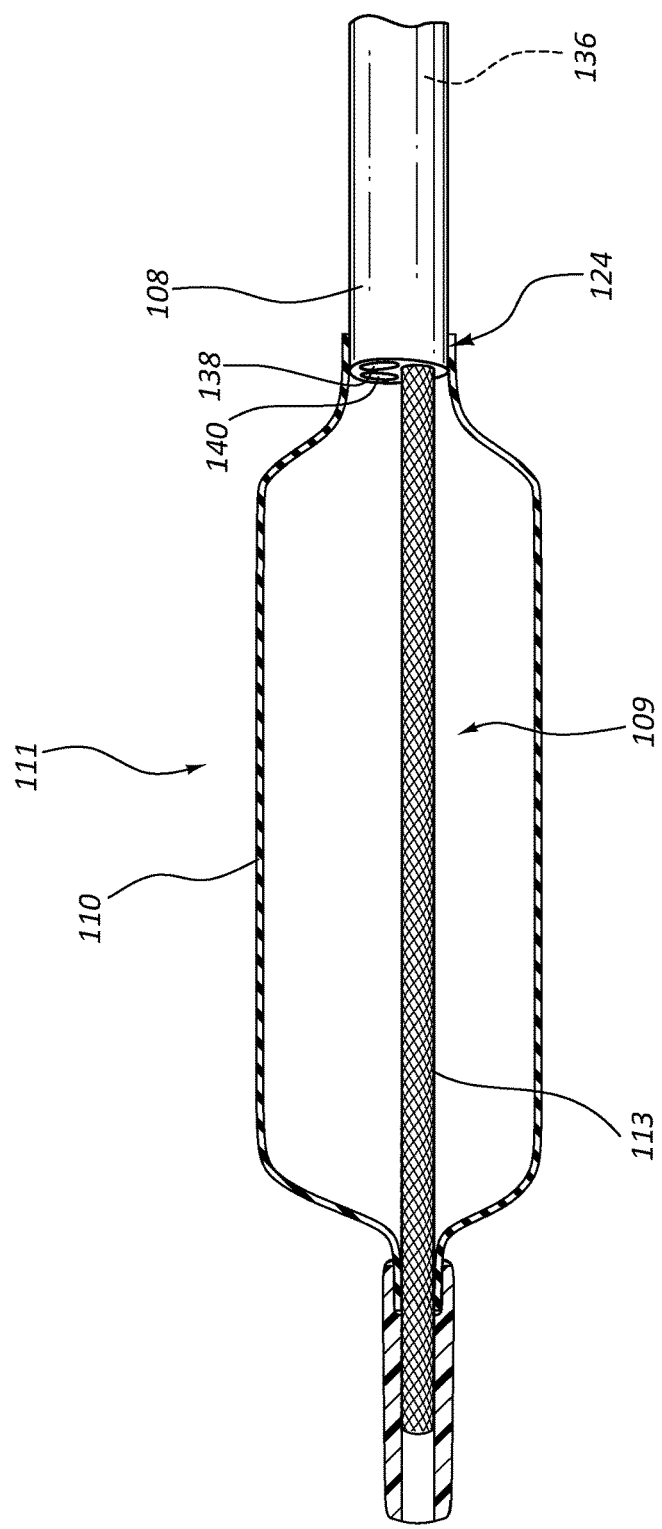
FIG. 7 is a partial cross-sectional view of the balloon segment of the balloon catheter assembly of FIG. 1.

FIG. 7 is a partial cross-sectional view of the balloon segment 111 of the balloon catheter assembly 100 of FIG. 1. As shown therein, the balloon segment 111 comprises an inflation balloon 110. The balloon segment 111 further comprises a tubular shaft 109 extending through the inflation balloon 110. The balloon segment 111 may be coupled to the distal end 124 of the elongated member 108. In some embodiments, for example, a guide wire lumen 136 of the elongated member 108 may be aligned with and coupled to the lumen of the tubular shaft 109. In such embodiments, the guide wire may be extended from the elongated member 108 through the inflation balloon 110 via the lumen of the tubular shaft 109. The tubular shaft 109 may isolate the guide wire lumen 136 of the elongated member 108 from lumens 138, 140 and an interior portion of the inflation balloon 110 such that inflation fluid from these areas does not leak into or flow through the guide wire lumen 136.

In some embodiments, the tubular shaft 109 comprises a reinforcement member 113. The reinforcement member 113 may comprise a braided structure. In other embodiments, the reinforcement member 113 may comprise a mesh or mesh-like structure. As illustrated in FIG. 7, the reinforcement member 113 may extend the length of the inflation balloon 110. In some embodiments, the reinforcement member 113 extends distally and/or proximally to a distance that is beyond the length of the inflation balloon 110. In other embodiments, the reinforcement member 113 extends only a portion of the length of the inflation balloon 110. In some embodiments, the reinforcement member 113 is constrained to the balloon segment 111 such that it does not extend the length of the elongated member 108.

The reinforcement member 113 may comprise a metal and/or polymeric material. The reinforcement member 113 may be disposed around the tubular shaft 109. In some embodiments, the reinforcement member 113 is coupled to the tubular shaft 109. In other embodiments, the reinforcement member 113 is not coupled to the tubular shaft 109. In some embodiments, the reinforcement member 113 is integral with the tubular shaft 109. In yet other embodiments, the reinforcement member 113 is embedded within a portion of the tubular shaft 109.

The reinforcement member 113 may provide strength, rigidity, and/or stiffness to the balloon segment 111. For example, in some embodiments, the reinforcement member 113 provides structural support for the tubular shaft 109. The added strength, rigidity, and/or stiffness may aid in inserting the balloon segment 111 through a body lumen. This strength can resist longitudinal compression of the inflation balloon 110 when it is advanced through a working channel or when it is deflated. The tendency of the tubular shaft 109 and reinforcement member 113 to hold their shape may thus reduce deformation of the balloon segment 111.

Use of a reinforcement member 113 also enables the manufacture of tubular shafts 109 having thinner walls and/or smaller diameters. Use of a reinforcement member 113 also provides support to the tubular shaft 109 during inflation of the inflation balloon 110. For example, the reinforcement member 113 may support the tubular shaft 109 to prevent collapsing as a result of the inflation pressure.

Figure 8:
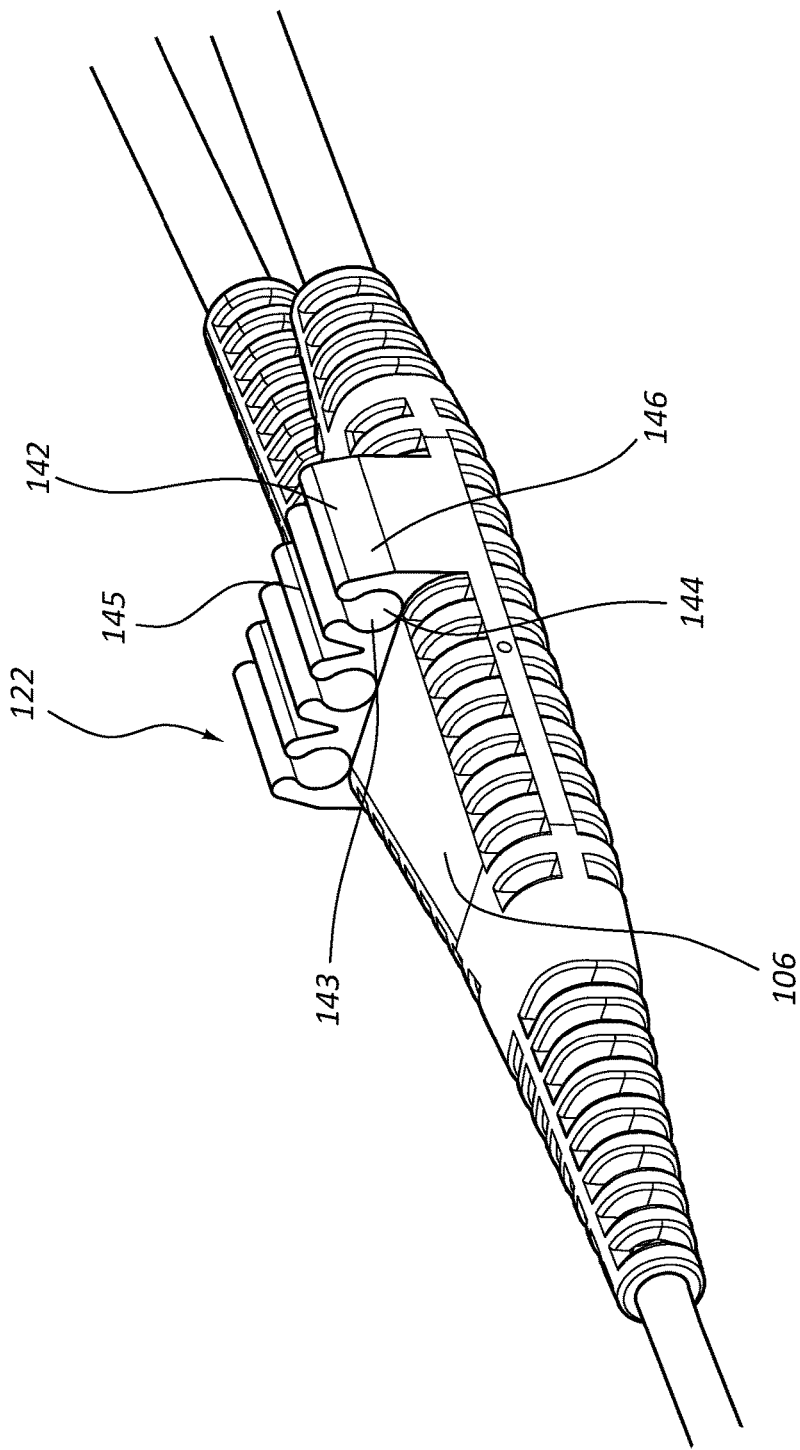
FIG. 8 is a perspective view of the retaining mechanism of the balloon catheter assembly of FIG. 1.
Figure 9:
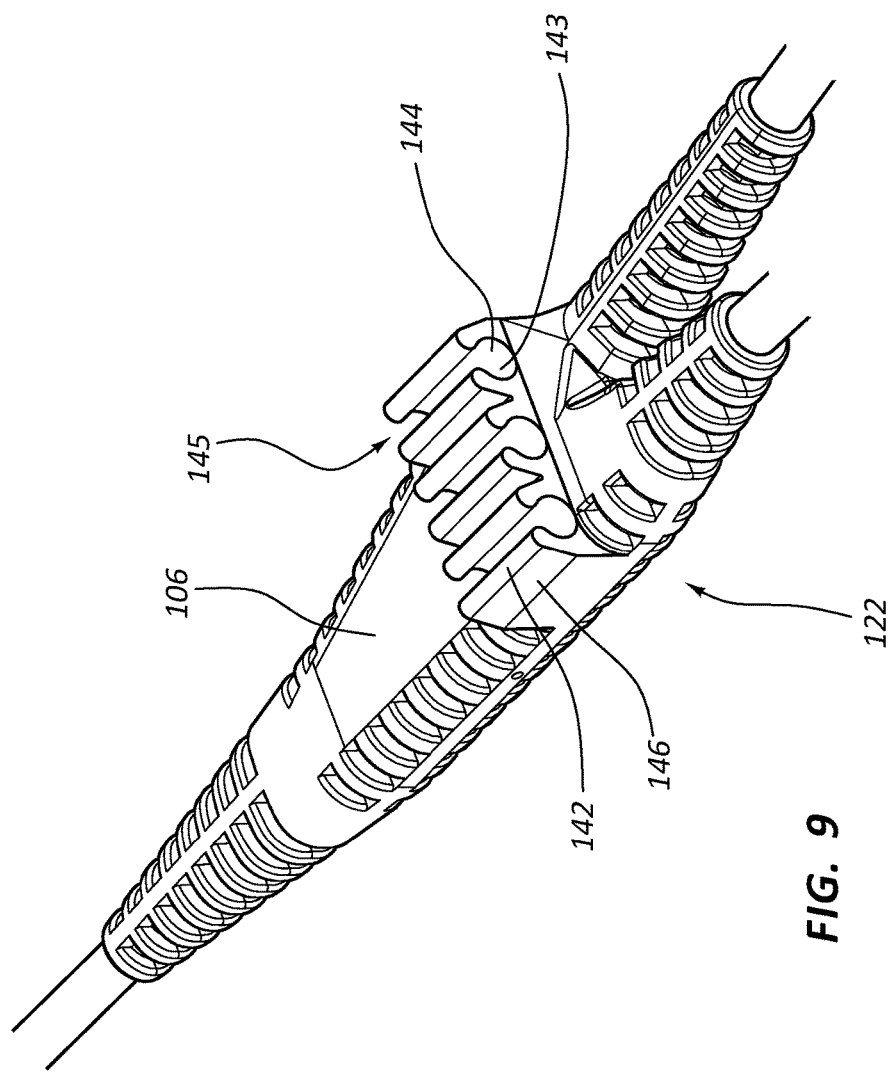
FIG. 9 is another perspective view of the retaining mechanism of the balloon catheter assembly of FIG. 1.

FIG. 8 is a perspective view of the retaining mechanism 122 of the balloon catheter assembly 100 of FIG. 1, and FIG. 9 is another perspective view of the retaining mechanism 122 of the balloon catheter assembly 100 of FIG. 1.

As shown in FIGS. 8 and 9, the retaining mechanism 122 may be coupled to or otherwise disposed on the junction hub 106. In some embodiments, the retaining mechanism 122 may be integral with the junction hub 106. In other embodiments, the retaining mechanism 122 may be removably attached or coupled to the junction hub 106 such that a practitioner may remove and/or discard the retaining mechanism 122 if desired.

The retaining mechanism 122 may also be coupled to other portions of the balloon catheter assembly, including a portion of the elongated member, catheter tubing, extension member(s), and/or other hubs. Further, the retaining mechanism 122 need not be limited to usage with the balloon catheter assemblies disclosed herein. Rather, the retaining mechanism 122 may be used in conjunction with any variety of catheter tubing known in the art or hereafter developed.

In the illustrated embodiments, the retaining mechanism 122 comprises a plurality of retaining members 142. In some embodiments, the retaining members 142 may be referred to as retaining clips. Any number of retaining members 142 may be used. For example, the illustrated retaining mechanism 122 comprises first, second, and third retaining members 142. In other embodiments, the retaining mechanism 122 comprises a single retaining member 142, or first and second retaining members 142. In yet other embodiments, the retaining mechanism 122 comprises four or more retaining members 142.

Each retaining member 142 comprises a channel 144 that is configured to receive and retain a portion of catheter tubing. The channel 144 comprises a seating region 143, and opposing or complimentary walls 146 that extend upwardly and inwardly toward one another. The interior sides of the walls 146 are also rounded. In some embodiments, the curvature of the interior sides of the walls 146 may be substantially the same as the curvature of the catheter tubing that the retaining member 142 is configured to retain. The walls 146 of the channel 144 are also biased toward an inwardly, or curved inwardly, retaining position. The biasing and/or compliance of the walls 146 toward the inwardly retaining position may create a snap fit with the catheter tubing that is to be retained.

In the illustrated embodiment, an elongated opening 145 across the channel 144 is narrower than the seating region 143 of the channel 144 that is configured to house the catheter tubing. The elongated opening 145 may also be narrower than the diameter of the catheter tubing. The walls 146 comprise a relatively soft polymeric material that is configured to flex and/or bend when a portion of the catheter tubing is forced or otherwise inserted through the elongated opening 145 of the channel 144. For example, the walls 146 may flex outwardly to expand the size or otherwise widen the elongated opening 145 during insertion and/or removal of the catheter tubing. In some embodiments, the catheter tubing may also be temporarily compressed as it is inserted through the elongated opening 145. After the catheter tubing is seated within the channel 144, the walls 146 of the retaining member 142 transition toward their inwardly biased position to retain the catheter tubing in a fixed position. As previously stated, this may be referred to as a snap fit, compliant fit, and/or compliance fit. In some embodiments, the catheter tubing may be described as being snugly retained by the retaining member 142 because the catheter tubing remains in a fixed position absent exertion of an external force on the catheter tubing.

In some embodiments, the catheter tubing may be wrapped and/or coiled, and a portion of the individual coils may be clipped, snapped, forced, pressed, or otherwise inserted into the channel 144 of one or more retaining members 142 to retain the catheter tubing in a coiled configuration. Prior to use, a practitioner may pull the catheter tubing outwardly through the elongated opening 145 of the channel 144, thereby removing the catheter tubing from its coiled configuration. If desired, the catheter tubing may be rewrapped and/or recoiled and snapped back into the channel 144 of one or more retaining members 142.

Figure 10:
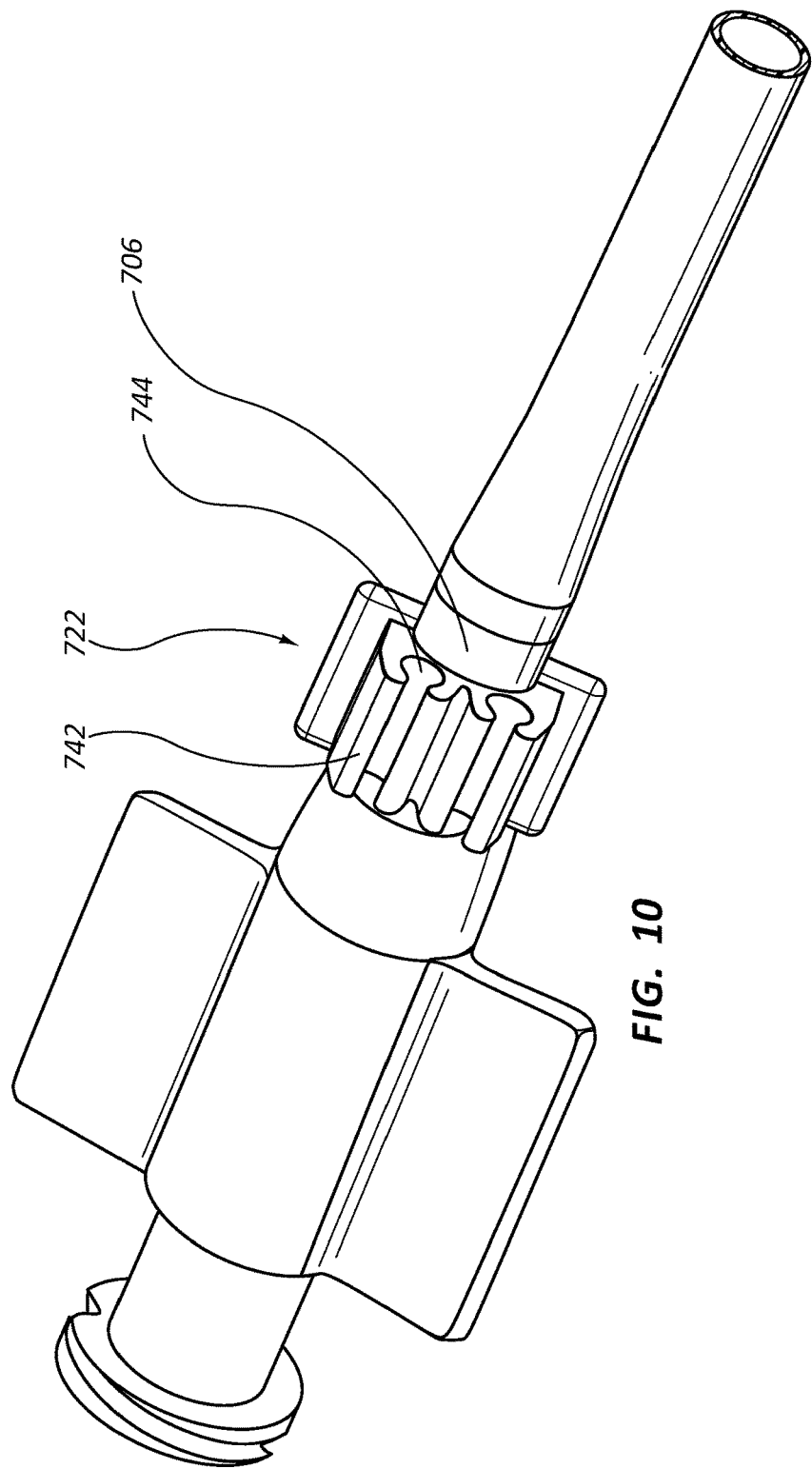
FIG. 10 is a perspective view of a retaining mechanism of a balloon catheter assembly, according to another embodiment of the present disclosure.
Figure 11:
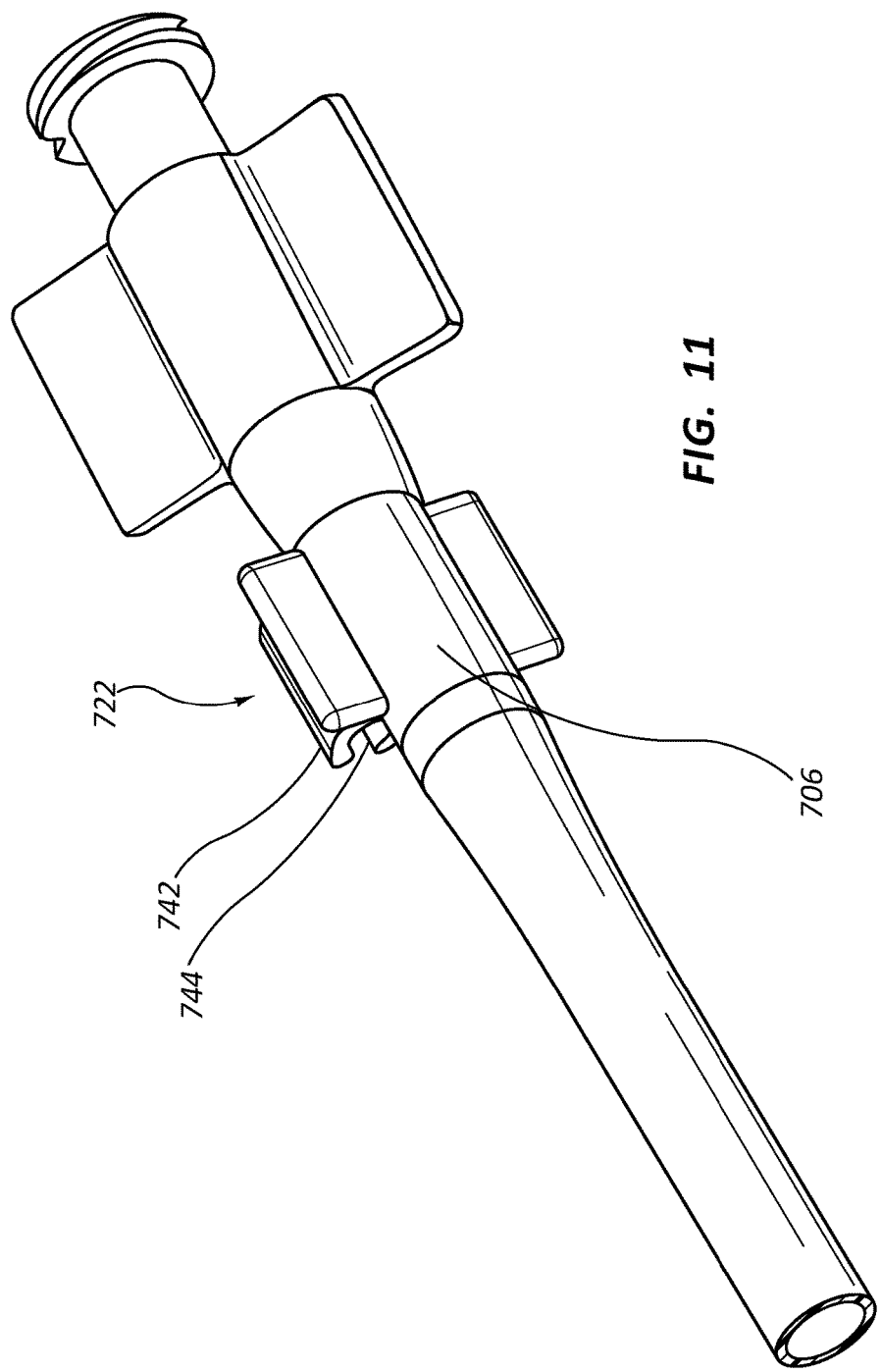
FIG. 11 is another perspective view of the retaining mechanism of FIG. 10.

FIG. 10 is a perspective view of a retaining mechanism 722 of a balloon catheter assembly, according to another embodiment of the present disclosure, and FIG. 11 is another perspective view of the retaining mechanism 722 of FIG. 10. The retaining mechanism 722 comprises two retaining members 742, each comprising a channel 744. The retaining mechanism 722 is further depicted as being disposed on a junction hub 706. Further, it is within the scope of this disclosure to include flanges or appendages to support the retaining mechanism 722, for example in embodiments wherein the junction hub 706 is not as wide as the desired width of the retaining mechanism. Further, it is within the scope of this disclosure for the retaining mechanism to be disposed on a rounded surface, such as around the circumference of the junction hub 706.

Figure 12:
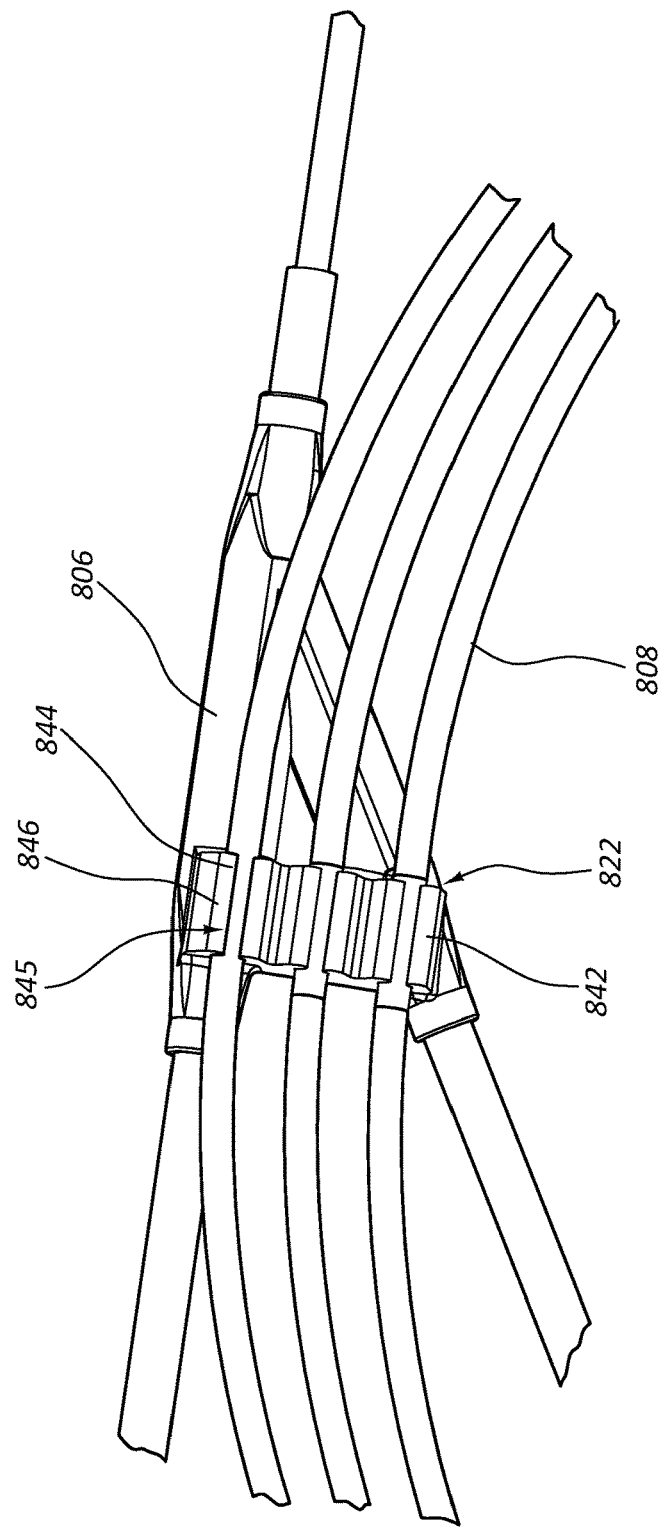
FIG. 12 is a perspective view of a retaining mechanism of a balloon catheter assembly, according to yet another embodiment of the present disclosure.

FIG. 12 is a perspective view of a retaining mechanism 822 according to yet another embodiment of the present disclosure. In FIG. 12, the retaining mechanism 822 is disposed on a junction hub 806. The catheter tubing or elongated member 808 is coiled and fixedly retained by the retaining mechanism 822. More specifically, portions of three coils of the catheter tubing or elongated member 808 are shown retained within individual retaining members 842. The walls 846 of the retaining members 842 are biased inwardly and create a compliance, compliant, or snap fit with the catheter tubing or elongated member 808. Prior to usage, a practitioner may pull the catheter tubing or elongated member 808 outwardly through the elongated openings 845 of the channels 844 to remove the catheter tubing or elongated member 808 from the retaining member 842.

Figure 13:
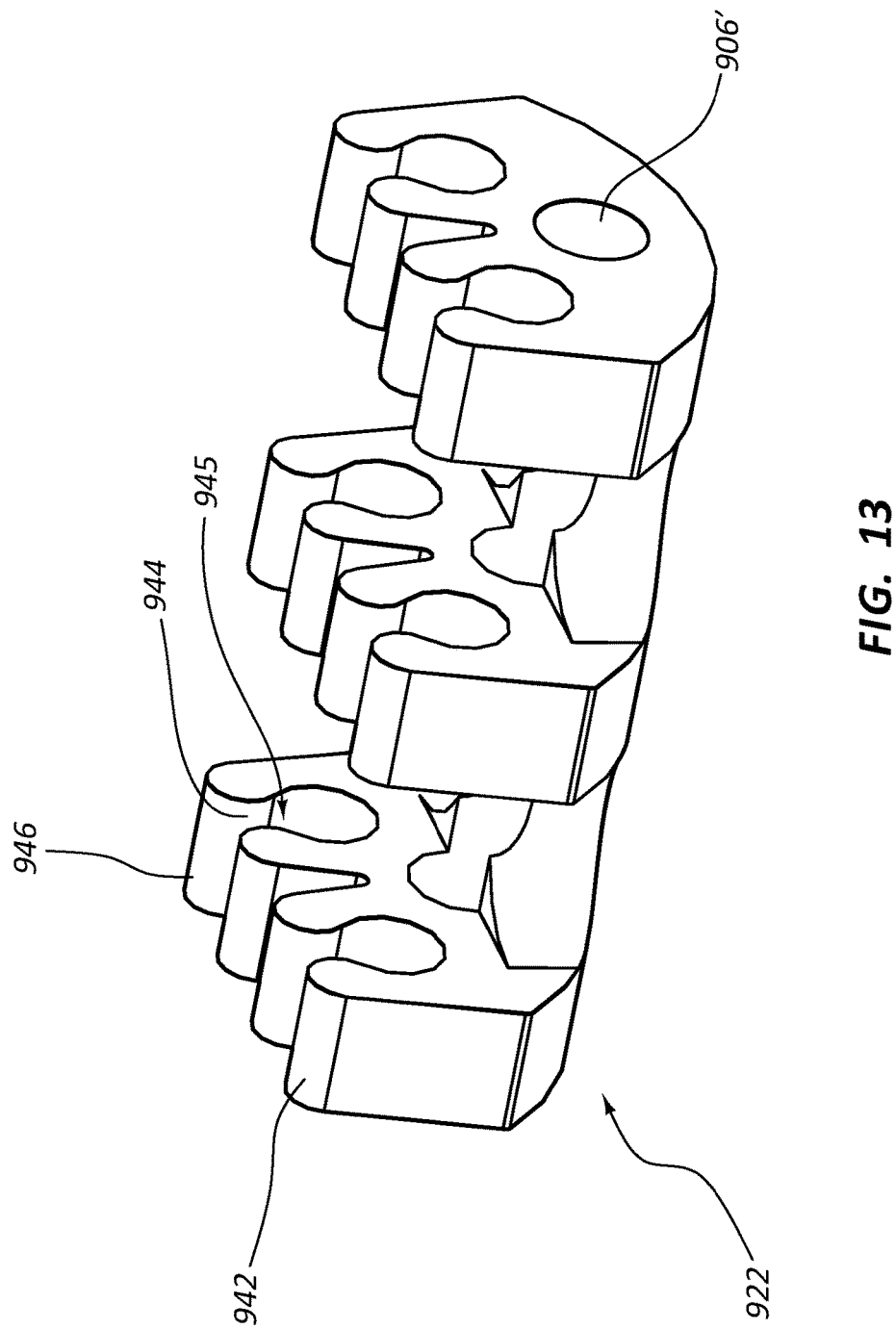
FIG. 13 is a perspective view of a retaining mechanism of a balloon catheter assembly, according to another embodiment of the present disclosure.

FIG. 13 is a perspective view of a retaining mechanism 922 of a balloon catheter assembly, according to another embodiment of the present disclosure. As with other embodiments, this embodiment comprises walls 946 of the retaining members 942 that are biased inwardly and create a compliance, compliant, or snap fit with the catheter tubing or elongated member. Prior to usage, a practitioner may pull the catheter tubing or elongated member outwardly through the elongated openings 945 of the channels 944 to remove the catheter tubing or elongated member from the retaining member 942. Further, in this embodiment, rather than direct mounting on a hub or other feature, the retaining mechanism 922 comprises a mounting channel 906'. A portion of an elongated member may be inserted into the mounting channel 906' coupling the retaining mechanism 922 to the assembly.

Figure 16:
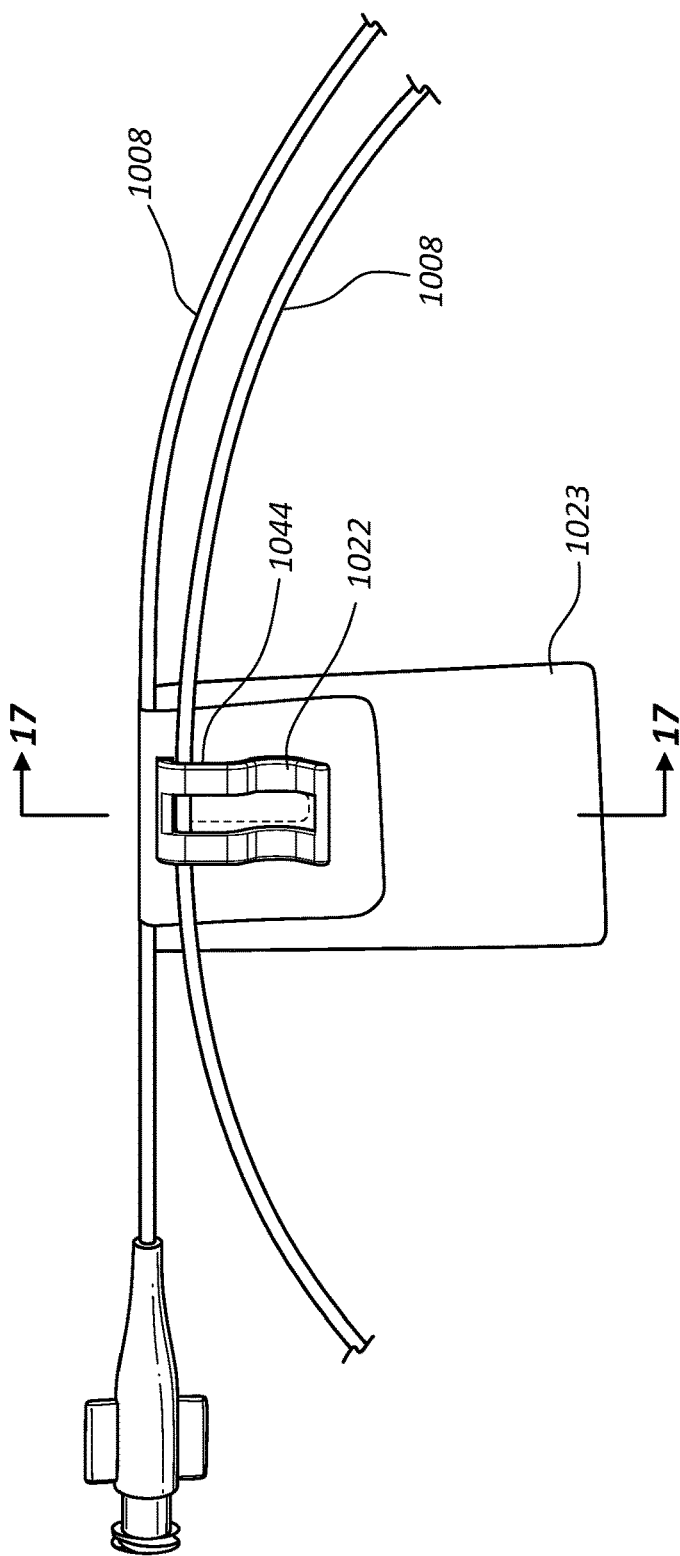
FIG. 16 is a side view of the assembly of FIG. 15 in a second configuration.
Figure 17:
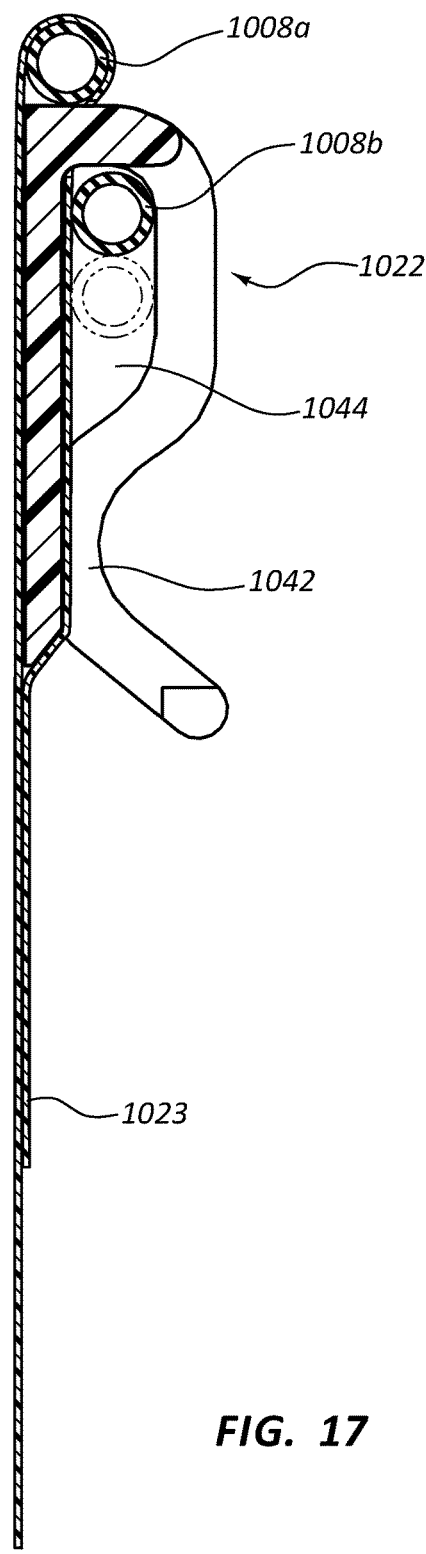
FIG. 17 is a cross-sectional view of the assembly of FIG. 16 taken through line 17-17.

FIGS. 14-17 are various views of another embodiment of a retaining mechanism 1022. Specifically, FIG. 14 is a perspective view of the retaining mechanism 1022 of a balloon catheter assembly; FIG. 15 is a side view of an assembly comprising the retaining mechanism 1022 of FIG. 14 and a portion of a balloon catheter assembly in a first configuration; FIG. 16 is a side view of the assembly of FIG. 15 in a second configuration; and FIG. 17 is a cross-sectional view of the assembly of FIG. 16 taken through line 17-17.

As shown in FIG. 14, the retaining mechanism 1022 may comprise a channel 1044 configured to retain portions of an elongated member. A retaining member 1042 may extend over the channel 1044. The retaining member 1042 may be sufficiently compliant to allow it to deform as an elongated member is inserted into the channel 1044, allowing the elongated member to be advanced into the channel 1044. As shown in FIGS. 15-17, the retaining mechanism 1022 may be coupled to a balloon catheter assembly including an elongated member 1008. A secondary member may be used to couple the retaining mechanism 1022 to the elongated member 1008. For example, in the illustrated embodiment, a label 1023 is coupled to both the retaining mechanism 1022 and the elongated member 1008. The retaining mechanism 1022 may be fixedly coupled to the elongated member 1008 at the secondary member, such as the label 1023, while removably coupled to the elongated member 1008 at other portions. For example, in the configuration of FIG. 15, the elongated member 1008 is not disposed within the channel 1044, while in the configuration of FIG. 16, a portion of the elongated member 1008 is disposed within the channel 1044. This is also shown in FIG. 17, wherein a portion of the elongated member 1008a is coupled to the label 1023 and the retaining mechanism 1022. A second portion of the elongated member 1008b is disposed within the channel 1044. A practitioner may remove this portion 1008b from the channel 1044, or insert a further portion of the elongated member into the channel 1044 (as shown by the broken lines) by displacing the retaining member 1042 to allow access to the channel 1044. While the elongated member 1008b is disposed in the channel 1004, pressure from the retaining member 1042 may slightly compress the elongated member 1008b.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially circular" is recited with respect to a feature, it is understood that in further embodiments, the feature can have a precisely circular configuration. Additionally, as used herein, a parameter or feature termed to be substantially equal to a value is within 10% of that value. Further, features that substantially correspond to a geometric shape are within 10% of that shape. Thus, the radii of a substantially circular feature do not vary by more than 10%, and so forth.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. The scope of the invention is therefore defined by the following claims and their equivalents.

What is claimed is:

1. A balloon catheter assembly, comprising:
   an elongated member comprising:
      a first lumen extending longitudinally through the elongated member, the first lumen in communication with a first proximal port;
      a second lumen extending longitudinally through the elongated member from a proximal end of the elongated member to a distal end of the elongated member; and
      a third lumen extending longitudinally through the elongated member from the proximal end of the elongated member to the distal end of the elongated member; and
      a junction hub disposed at the proximal end of the elongated member comprising:
         a first extension member in fluid communication with the first lumen; and
         a second extension member in fluid communication with the second and third lumens, wherein a lumen of the second extension member is bifurcated to form the second and third lumens; and
   a balloon segment comprising:
      an inflation balloon coupled to the elongated member such that an interior portion of the inflation balloon is in fluid communication with the second lumen and the third lumen but is not in fluid communication with the first lumen;
      a tubular shaft extending through the inflation balloon, wherein the tubular shaft is aligned with and coupled to the first lumen, the tubular shaft configured such that a guide wire is extendable from the first lumen of the elongated member to the tubular shaft and through the inflation balloon; and a reinforcement member coupled to a portion of the tubular shaft, wherein the reinforcement member is constrained to the balloon segment.

2. The balloon catheter assembly of claim 1, wherein the first lumen is substantially circular in shape and the second and third lumens are substantially elliptical in shape.

3. The balloon catheter assembly of claim 1, wherein the first lumen is substantially circular in shape and the second and third lumens are substantially kidney shaped.

4. The balloon catheter assembly of claim 1, wherein:

a cross-section of the elongated member defines a vertical axis and a horizontal axis disposed perpendicular to the vertical axis;

a cross-section of the first lumen is substantially centered along the vertical axis; and a cross-section of the second lumen and a cross-section of the third lumen are each substantially elliptical in shape, wherein a major axis of the second lumen and a major axis of the third lumen are disposed at substantially 45 degrees to the horizontal axis of the cross-section of the elongated member.

5. The balloon catheter assembly of claim 4, wherein a portion of the second lumen and a portion of the third lumen each intersect the horizontal axis of the cross-section of the elongated member.

6. The balloon catheter assembly of claim 4, wherein the cross-section of the first lumen and the cross-section of the elongated member are each substantially circular.

7. The balloon catheter assembly of claim 6, wherein the minimum dimension of any wall disposed between the first, second, and third lumens or any wall disposed between the first, second, and third lumens and the circumference of the elongated member is no less than 10% of a diameter of the cross-section of the elongated member.

8. The balloon catheter assembly of claim 6, wherein a diameter of the cross-section of the first lumen is no more than 50% of a diameter of the cross-section of the elongated member.

9. The balloon catheter assembly of claim 6, wherein a minor axis of the second lumen is no more than 40% of a diameter of the cross-section of the elongated member, and a minor axis of the third lumen is no more than 40% of the diameter of the cross-section of the elongated member.

10. The balloon catheter assembly of claim 1, wherein the sum of an area circumscribed by the cross-section of the second lumen and an area circumscribed by the cross-section of the third lumen is between 1.4 and 2 times an area circumscribed by the cross-section of the first lumen.

11. The balloon catheter assembly of claim 1, wherein the reinforcement member comprises a braided structure.

12. The balloon catheter assembly of claim 1, wherein the reinforcement member is disposed such that it resists longitudinal compression of the inflation balloon.

13. The balloon catheter assembly of claim 12, wherein the reinforcement member and tubular shaft exert a longitudinal expansion force on the inflation balloon when the inflation balloon is in a deflated configuration.

14. The balloon catheter assembly of claim 1, wherein the first lumen is in direct communication with the tubular shaft.

15. The balloon catheter assembly of claim 1, wherein the reinforcement member is integral with the tubular shaft.

16. The balloon catheter assembly of claim 1, wherein the reinforcement member is embedded within a portion of the tubular shaft.

* * * * *